United States Patent
Yin et al.

(10) Patent No.: US 11,786,202 B2
(45) Date of Patent: **\*Oct. 17, 2023**

(54) METHOD, SYSTEM, AND MEDIUM FOR ANALYZING IMAGE SEQUENCE OF PERIODIC PHYSIOLOGICAL ACTIVITY

(71) Applicant: SHENZHEN KEYA MEDICAL TECHNOLOGY CORPORATION, Shenzhen (CN)

(72) Inventors: Youbing Yin, Kenmore, WA (US); Shubao Liu, College Park, MD (US); Qi Song, Seattle, WA (US); Ying Xuan Zhi, Seattle, WA (US)

(73) Assignee: SHENZHEN KEYA MEDICAL TECHNOLOGY CORPORATION, Shenzhen (CN)

( * ) Notice: Subject to any disclaimer, the term of this patent is extended or adjusted under 35 U.S.C. 154(b) by 272 days.

This patent is subject to a terminal disclaimer.

(21) Appl. No.: 17/219,957

(22) Filed: Apr. 1, 2021

(65) Prior Publication Data
US 2021/0219934 A1 Jul. 22, 2021

Related U.S. Application Data

(63) and a continuation-in-part of application No. 16/689,048, filed on Nov. 19, 2019, now Pat. No.
(Continued)

(51) Int. Cl.
*A61B 6/00* (2006.01)
*G06T 7/20* (2017.01)
(Continued)

(52) U.S. Cl.
CPC .......... *A61B 6/504* (2013.01); *A61B 6/5217* (2013.01); *G06T 7/0012* (2013.01);
(Continued)

(58) Field of Classification Search
CPC ..... A61B 6/504; A61B 6/5217; A61B 6/5264; G06T 7/0012; G06T 7/0016; G06T 7/20;
(Continued)

(56) References Cited

U.S. PATENT DOCUMENTS 7,043,063 B1   5/2006 Noble et al.
10,229,504 B2   3/2019 Bigioi et al.
(Continued)

OTHER PUBLICATIONS

Maria J. Ledesma-Carbayo et al., "Spatio-Temporal Nonrigid Registration for Ultrasound Cardiac Motion Estimation," IEEE Transaction on Medical Imaging, vol. 24, No. 9 (Sep. 2005), pp. 1113-1126.
(Continued)

*Primary Examiner* — Siamak Harandi
(74) *Attorney, Agent, or Firm* — Bayes PLLC

(57) ABSTRACT

The disclosure relates to a computer-implemented method for analyzing an image sequence of a periodic physiological activity, a system, and a medium. The method includes receiving the image sequence from an imaging device, and the image sequence has a plurality of images. The method further includes identifying at least one feature portion in a selected image, which moves responsive to the periodic physiological activity. The method also includes detecting, by a processor, the corresponding feature portions in other images of the image sequence and determining, by the processor, a phase of a the selected image in the image sequence based on the motion of the feature portion.

20 Claims, 7 Drawing Sheets

Related U.S. Application Data 10,980,502, which is a continuation of application No. 15/864,398, filed on Jan. 8, 2018, now Pat. No. 10,499,867.

(60) Provisional application No. 63/081,276, filed on Sep. 21, 2020.

(51) Int. Cl.
  *G06T 7/277* (2017.01)
  *G06T 7/00* (2017.01)
  *G06T 7/269* (2017.01)
  *G06F 16/50* (2019.01)

(52) U.S. Cl.
  CPC .............. *G06T 7/0016* (2013.01); *G06T 7/20* (2013.01); *G06T 7/269* (2017.01); *G06T 7/277* (2017.01); *A61B 6/5264* (2013.01); *G06F 16/50* (2019.01); *G06T 2207/10081* (2013.01); *G06T 2207/30004* (2013.01); *G06T 2207/30048* (2013.01); *G06T 2207/30101* (2013.01)

(58) Field of Classification Search
  CPC ............. G06T 7/269; G06T 7/277; G06T 2207/10081; G06T 2207/30004; G06T 2207/30048; G06T 2207/30101; G06T 7/246; G06F 16/50; G06F 16/535; G16H 30/40; G16H 50/20; G16H 50/30
  See application file for complete search history.

(56) References Cited

U.S. PATENT DOCUMENTS

| | | |
|---|---|---|
| 10,499,867 B2 | 12/2019 | Liu et al. |
| 2005/0107704 A1 | 5/2005 | Von Behren et al. |
| 2005/0201604 A1* | 9/2005 | Hristov ............... G06T 11/008 382/284 |
| 2005/0215904 A1 | 9/2005 | Sumanaweera et al. |
| 2008/0051660 A1 | 2/2008 | Kakadaris et al. |
| 2008/0095417 A1 | 4/2008 | Pedrizzetti et al. |
| 2010/0020244 A1 | 1/2010 | Mitsuya et al. |
| 2013/0034272 A1 | 2/2013 | Thomas |
| 2013/0116739 A1 | 5/2013 | Brada et al. |
| 2014/0334697 A1 | 11/2014 | Kersten et al. |
| 2016/0180546 A1 | 6/2016 | Kim et al. |
| 2016/0210747 A1 | 7/2016 | Hay et al. |
| 2016/0253820 A1 | 9/2016 | Jeanne et al. |

OTHER PUBLICATIONS

Bruce D. Lucas Takeo Kanade, "An Iterative Image Registration Technique with a Application to Stereo Vision," Proceedings of Imaging Understanding Workshop (1981), pp. 121-130.

Berthold K.P. Horn & Brian G. Schunck, "Determining Optical Flow," Artificial Intelligence, vol. 17 (1981), pp. 185-203.

Gunnar Farneback, "Two-Frame Motion Estimation Based on Polynomial Expansion," Scandinavian Conference on Image Analysis (2003), pp. 363-370.

Bernhard Scholkopf et al., "Kernel Principal Component Analysis," International Conference on Artificial Neural Networks (1997), pp. 583-588.

Geoffrey E. Hinton et al., "A Fast Learning Algorithm for Deep Belief Nets," Neural Computation, vol. 18 (2006), pp. 1527-1554.

* cited by examiner

METHOD, SYSTEM, AND MEDIUM FOR ANALYZING IMAGE SEQUENCE OF PERIODIC PHYSIOLOGICAL ACTIVITY

CROSS REFERENCE TO RELATED APPLICATIONS

This application is a continuation-in-part of U.S. patent application Ser. No. 16/689,048, filed on Nov. 19, 2019, which is a continuation of U.S. patent application Ser. No. 15/864,398, filed on Jan. 8, 2018, now issued as U.S. Pat. No. 10,499,867 on Dec. 10, 2019, and claims the benefit under 35 U.S.C. § 119(e) of U.S. Provisional Application No. 63/081,276, filed on Sep. 21, 2020, all of which are incorporated herein by reference in their entireties.

TECHNICAL FIELD

The present disclosure relates to a method, a system, and a computer storage medium for analyzing an image sequence of a periodic physiological activity. For example, the disclosure relates to a method, a system, and a computer storage medium for obtaining phase information by analyzing image sequences of periodic physiological activities.

BACKGROUND

Many physiological activities, such as respiration and cardiac motion, exhibit cyclic patterns. The phase information of each individual frame in an image sequence of a periodic physiological activity provides potentially useful information for medical imaging and diagnostics. For example, when interpreting pulmonary computerized tomography (CT) images, physicians may wish to discriminate between the inspiratory and expiratory phases, corresponding to breathing in and breathing out. In addition, these periodic movements are important for synchronizing frames of image sequences of the physiological activities. For example, during a reconstruction of 3-dimensional (3-D) physiological structures from 2-dimensional (2-D) images acquired from different scanning angles, it is helpful to keep the phase of the respective 2-D images at their own individual angles to have the same phase in the periodic physiological activity. Such an approach potentially minimizes the impact of tissue deformations that may otherwise occur at different phases on the result of 3-D reconstruction. Furthermore, in cardiovascular disease diagnosis and intervention, accurately determining the phase of an individual frame in the cardiac period facilitates deriving other important physiological parameters, such as heart rate, cardiac period, and so on. Determining such physiological parameters may provide insight about health information, in that such physiological parameters may be indicators of potential good health or of potential health problems.

X-ray coronary angiography (CAG) is a procedure that uses contrast dye during X-ray imaging to better distinguish vessel structures from other tissues. Such a contrast dye may be a radiocontrast agent, such as iodine, gadolinium, or barium sulfate, as non-liming examples. In CAG, the vascular structure is often captured in video sequences obtained from several different angles of X-ray projections. Based on CAG, medical imaging applications are being developed to extract vascular physiological structures and obtain associated physiological parameters (such as volume and diameters of a blood vessel, which may be an artery or a vein). These results permit the medical imaging applications to reconstruct 3-D vessel structures, and also to simulate functional hemodynamics. A functional hemodynamics simulation is generally used to assess an influence of vascular lesions on a subject's blood supply. A shape deformation of coronary vessels during heartbeats, may occur as the heart pumps. Accordingly, an automatic and accurate acquisition of corresponding periodic phases of each individual frame in the image sequence acquired from different scanning angles is critical for an accurate estimation of vascular feature parameters and successful synchronization of image frames for reconstruction.

Traditionally, additional periodic monitoring devices such as electrocardiograms (ECGs) and respiratory monitors are typically used to record and monitor relevant clinical information in clinical practice. However, those devices do not come standard as being integrated into a corresponding imaging system setup in a hospital. Introducing additional equipment requires extra physical space and time and attention from physicians to compare between the periodic monitoring device and the imaging system. Without the presence of cardiac monitoring signals (for example, a synchronizing electrocardiogram gating signal/ECG), a manual identification of the correlation between image frames and their cardiac periodic phases is often time-consuming. It is also potentially difficult for the identification of the correlation to be accurate. Currently, there are several main analysis methods to estimate cardiac cyclic phases based on image sequences of vessels. One method involves calculating the difference between different frames (for example, consecutive frames) and identifying the time window with the slowest phase change, so as to utilize several image frames in that identified time window for analysis. Such a method does not estimate the phase of each frame. This method also does not discriminate between a diastole phase and a systole phase. The method is also sensitive to the background noise in the images. Another possible method depends on comparison with reference frames to determine the phases. This method requires a manual selection of the reference image for the desired phase or requires that the reference images in the database are highly consistent with the current image sequence. Similar problems may occur when the above analysis methods are applied to image sequences of periodic physiological activities other than cardiac cycle, such as lung activity occurring in a respiratory cycle.

Thus, typical methods for analyzing periodic phases have issues, as follows. Such methods either rely on additional periodic monitoring devices or, alternatively, on manually picked reference images. These aspects of typical methods increase the complexity of the system and the labor and time burden on clinicians. Further, typical methods usually require calculating all of the individual pixels in each frame of the image sequence and estimate the phase of each frame in the periodic motion based on the calculation results. Such an approach increases the computational load. Further, the periodic motion is highly sensitive to background noise in the images or may be submerged in or attenuated by other motions and noises. Thus, the analysis results from typical methods are susceptible to a lack of accuracy.

The present application has been proposed to solve the above-identified problems as well as for other advantageous purposes.

SUMMARY

Certain embodiments may provide a method and a system for efficient and accurate estimation for phases using image frames, based on the inherent dynamic changes of the image sequence of the periodic physiological activities. Such a method and system may get rid of inefficient operations on each pixel. The method and system may also reduce efficiently the interference from noises and other motions on the periodic physiological activity. Consistent with the disclosure, a "frame" can be a 2-D image when the image sequence is a 3-D image sequence (a sequence of 2-D images over time) or a 3-D image when the image sequence is a 4-D image sequence (a sequence of 3-D images over time).

The embodiments according to the disclosure adopt the following technical schemes, at least to solve the technical problems mentioned above.

According to a first aspect of the present disclosure, there is provided a computer-implemented method for analyzing an image sequence of a periodic physiological activity. The computer-implemented method begins with receiving the image sequence acquired by an imaging device, where the image sequence includes a plurality of images. Then, at least one feature portion is identified in an image of the image sequence, the at least one feature portion moving responsive to the periodic physiological activity. Next, the following process is performed by a processor: detecting the corresponding feature portions in other images of the image sequence, and determining a phase of a selected image in the image sequence based on the motion of the feature portion.

According to a second aspect of the present disclosure, there is provided a system for analyzing an image sequence of periodic physiological activity. The system includes an interface and a processor. In the system, the interface is configured to receive the image sequence acquired by an imaging device, and the image sequence includes a plurality of images. The processor is configured to perform the following steps. At least one feature portion, which moves responsive to the periodic physiological activity, may be identified in an image of the image sequence. Then, the corresponding feature portions may be detected in other images of the image sequence. A phase of a selected image in the image sequence may be determined based on the motion of the feature portion.

According to a third aspect of the present disclosure, there is provided a non-transitory computer-readable storage medium, with computer-executable instructions stored thereon. The instructions, when executed by a processor, cause the processor to perform a method for analyzing an image sequence of a periodic physiological activity according to each embodiment of the present disclosure, corresponding to the method described above.

Each embodiment of the disclosure has at least the following beneficial effects. An embodiment makes a calculation for the motion of specific feature portions within images in the image sequence of periodic physiological activities. Such an embodiment does not need to make calculations for the motions of all pixels (including each individual pixel) in each image of the image sequences. Consequently, the computational load is reduced and the processing efficiency is improved.

BRIEF DESCRIPTION OF THE DRAWINGS

In the drawings, which are not necessarily drawn to scale, like reference numerals may describe similar components in different views. Like reference numerals having letter suffixes or different letter suffixes may represent different instances of similar components. The drawings illustrate generally, by way of example, but not by way of limitation, various embodiments, and together with the description and claims, serve to explain the disclosed embodiments. Such embodiments are demonstrative and not intended to be exhaustive or exclusive embodiments of the present method, device, system, or non-transitory computer readable medium having instructions thereon for implementing the method.

DETAILED DESCRIPTION

Figure 1:
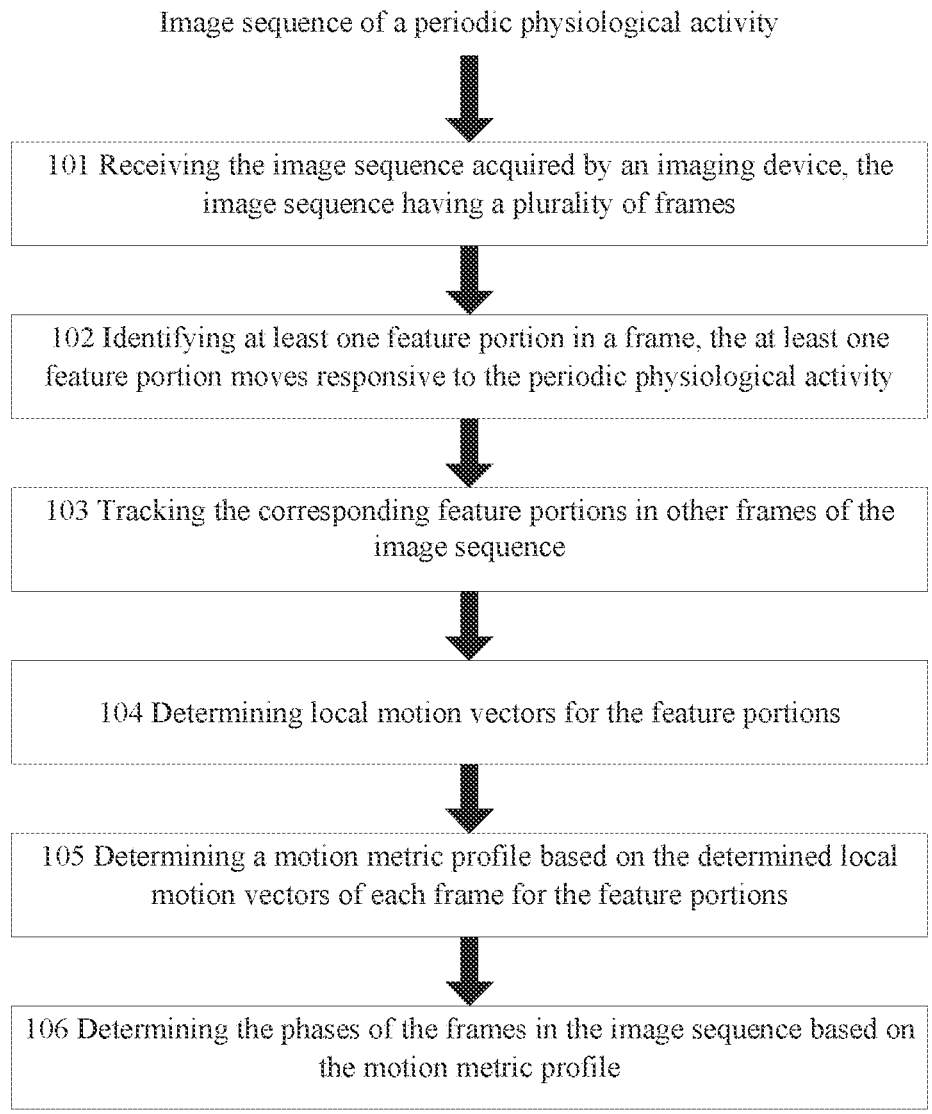
FIG. 1 illustrates a flowchart of a method for analyzing an image sequence of a periodic physiological activity according to an embodiment of the present disclosure.

FIG. 1 illustrates a flowchart of a method for analyzing an image sequence of a periodic physiological activity according to an embodiment of the present disclosure. As shown in FIG. 1, the method may begin with receiving an image sequence acquired by an imaging device, in which the image sequence has multiple frames, at operation 101. The following operations may then subsequently be performed by the processor. At least one feature portion that moves in response to said periodic physiological activity may be identified in a frame at operation 102. There is no special qualification for this frame, provided it is adapted to identify feature portions. As an example, a frame with a good filling effect and clear image development may be used in vessel angiographic images as a frame for identifying feature portions. The corresponding feature portions may be tracked in other frames of the image sequence, at operation 103. Subsequently, the phase of the respective frames in the image sequence may be determined based on the motion of the identified and tracked feature portions. As an example, the motion characteristic information, which is presented by feature portions across the image sequence, may be tracked so as to determine the phase of individual frames throughout the whole image sequence. The motion characteristic information may include motion profile or a motion parameter such as velocity, acceleration, and so on, but these are only non-limiting examples.

Operations 104 through 106 illustrate an example of a procedure for determining the phase of each frame in the image sequence based on the motion of the feature portion, but it is to be noted that the implementation of such a procedure is not limited to these particular operations. Thus, a procedure for determining the phase of each frame may include all or some of operations 104, 105, and 106, as well as other operations. A local motion vector of the feature portion may be determined for each frame, at operation 104. Based on the local motion vector of the feature portion determined for each frame, the motion metric profile may be determined, at operation 105. Based on the motion metric profile, the phases of the frames in the image sequence may be determined, at operation 106.

Hereinafter, embodiments using each operation performed in the method are described in further detail.

Feature Portion Selection

First, an image sequence acquired by imaging device may be received, where the image sequence may have a plurality of frames. Then, at least one feature portion may be identified from a single frame selected from the received image sequence, and the at least one feature portion may also move responsive to the periodic physiological activity. For example, these portions of the method occur at operation 101 and operation 102.

A feature portion could be one or more points or areas in one or more regions of interest in the image, as a non-limiting example. For example, the feature portion may be areas corresponding to anatomical structures that move in synchronization with the periodic physiological activity. For example, the feature portion may be a heart, one or both lungs of a subject, or a portion or even a point of such organs. As a result, the feature portion may exhibit cyclic motion patterns during periodic physiological activities, such as cardiac cycles where the feature portion is all or part of a heart. Similarly, the feature portion may exhibit cyclic motion portions during respiration where the feature portion is one or both lungs, or a portion of one or both lungs.

In the selected frame of the image sequence, the points or areas with image features, which may be distinguished, detected, or tracked easily, may be selected as feature portions. Here, the selected frame is the frame in which the feature portion is identified. The relevant image features may include brightness, texture, and curve edges, as non-limiting examples. In some embodiments, the least one feature portion may include multiple critical areas. Additionally, a specific area of another object in the frame of the image sequence may be identified as the feature portion. For example, such a specific area may include, but is not limited to, implanted devices.

Figure 2A:
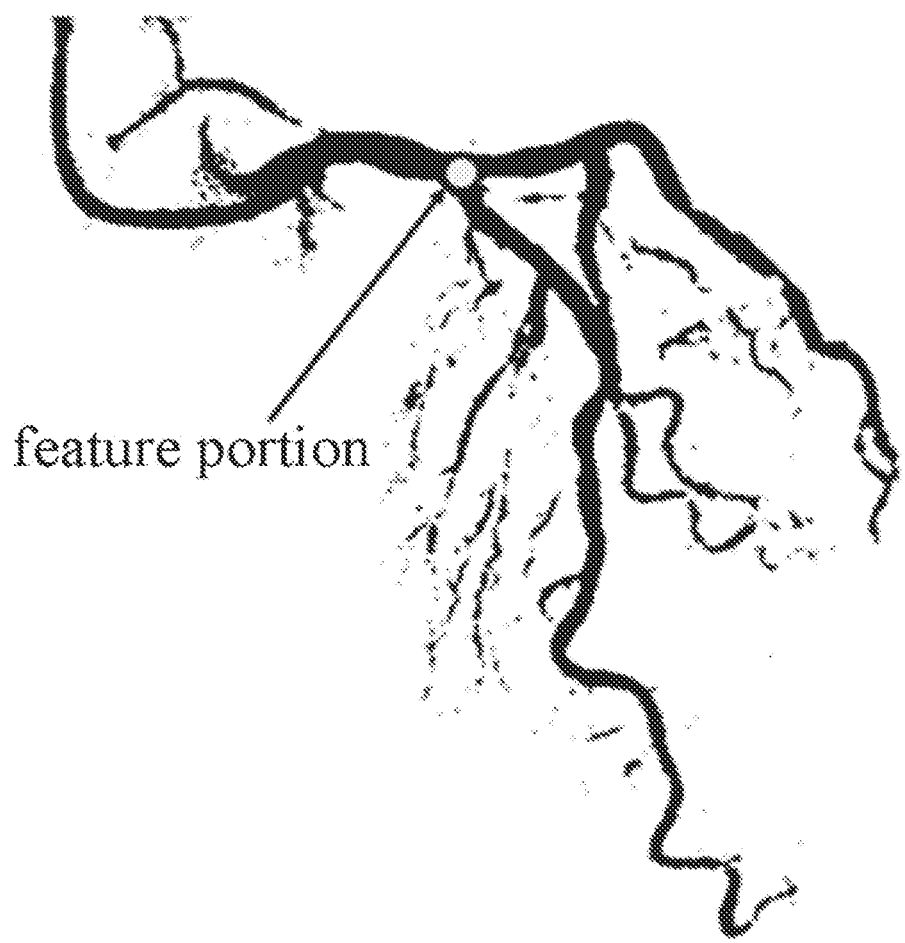
FIG. 2A and FIG. 2B illustrate schematic diagrams of feature portions selected according to an embodiment of the present disclosure.
Figure 2B:
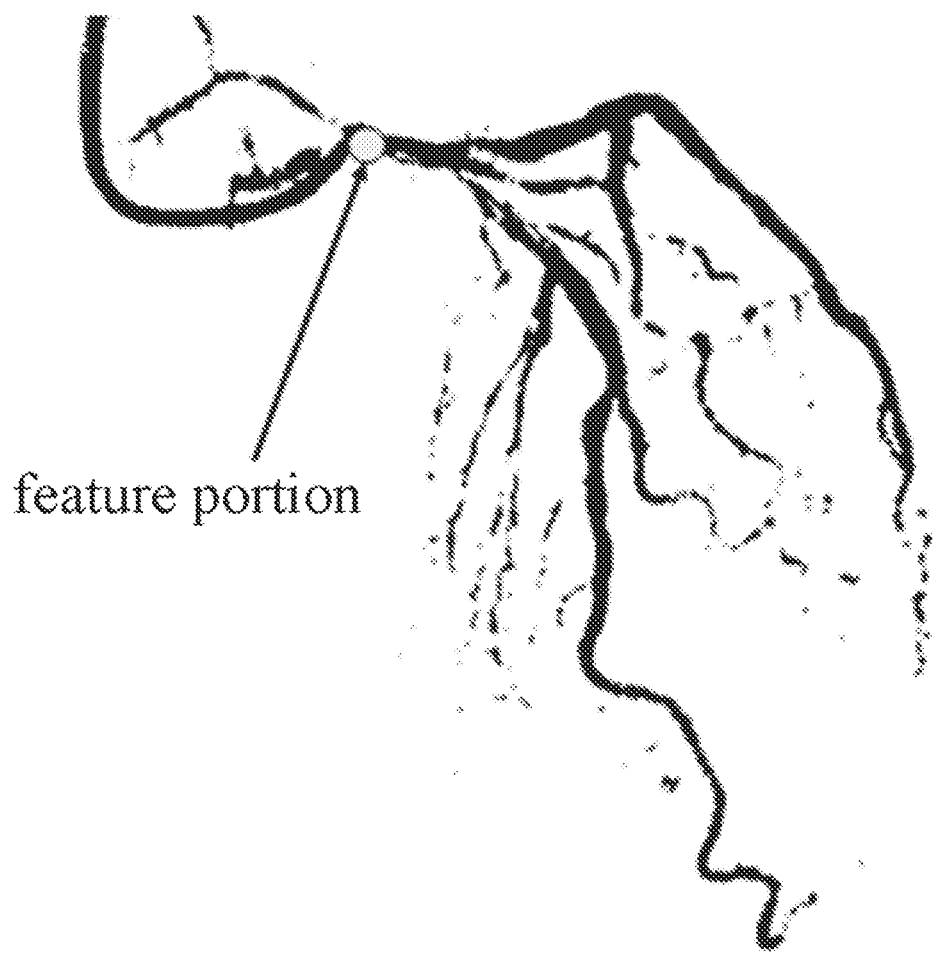

FIG. 2A and FIG. 2B show schematic diagrams of the feature portions selected according to the embodiments of the present disclosure.

In some embodiments, such as in the angiography as shown in FIG. 2A, the anatomical structure such as a vessel bifurcation may be selected as the feature portion. The vessel bifurcation may refer to a portion of a blood vessel where a primary artery branches out into several secondary vessels. Because a coronary artery only contains a few bifurcating points, and also in view of the unique geometric structure of vessel bifurcation, the vessel bifurcations may be easily distinguished from the other parts of the vessel. Therefore, utilizing of a vessel bifurcation as feature portion may facilitate the detection and tracking.

In other embodiments, as shown in FIG. 2B, the specific region of an intervention component, such as the tip of a catheter as a non-limiting example, may be used as the feature portion. Here, the catheter is a device that is inserted into the entrance of a blood vessel to enable the contrast agent injection. Because the catheter generally uses a certain model and shape, it may be discerned easily from the rest of the vessel. Specifically, in an example where the catheter is inserted into the vessel, the tip of the catheter abuts against the vessel and may be discerned easily from the vessel. For example, the catheter may have distinctive image features such as brightness, texture, curve edge, as non-limiting examples. Additionally, the tip of the catheter may follow the motion such as periodic motion of the vessel according to a similar time scheme, thus the tip of the catheter may exhibit cyclic motion patterns of the vessel.

It is to be noted that different feature portions may also be utilized in different applications, which are not limited to the examples illustrated above.

One feature portion may be selected, or alternatively, multiply feature portions may be selected, as required. In addition, the selection of the feature portion may be performed by means of automatic identification or selected by a user manually from a particular selected frame of an image sequence.

By means of selection of the feature portion, only the motion of specific feature portions out of images in the image sequence of periodic physiological activity are required to be calculated. In this manner, embodiments do not need to make calculations for motions of all pixels (that is, for each pixel) in the image. Consequently, the computational load is reduced and the processing efficiency is improved.

Feature Portion Tracking

Thereafter, a CAG image is taken as an example of image, one or more feature points are taken as an example of the feature portion, and a cardiac period is taken as an example of periodic physiological activity. It is to be noted that this disclosure is not limited to the particular examples illustrated above, but can also be adapted to other image types, other structures of feature portions, for example, multiple points or critical areas, and so on, as well as other types of periodic physiological activities such as respiration. A discussion of embodiments that are similar to the above discussion is not repeated to avoid redundancy.

After identifying the feature point in a frame selected out of the image sequence, the corresponding feature points in other frames of the image sequence may be tracked. That is, the position of the feature points in other image frames may be determined, i.e., $(x_i^t, y_i^t)$. Here i represents the feature point index and t represents the frame index. This operation may be referred as feature point tracking. Upon determining the position $(x_i^t, y_i^t)$ of the feature points presented in each frame of the image sequence, the motion vector of the feature point of the previous frame compared to the next frame out of the adjacent frames may be calculated as a local motion vector of the feature point for each frame. It is to be noted that the term "local motion vector" is merely used to be distinguished from the principal motion vector after principal component analysis, which actually indicates the motion vectors of the feature point among individual frames.

Feature point tracking may be implemented by using different approaches. As examples, the following two methods may be adopted. The first method includes establishing a statistical model of feature points and then tracking the corresponding feature points independently in each frame, based on the corresponding statistical model. Such a statistical model-based tracking approach is stable in the sense that it does not accumulate drifting error along the image sequence and does not fail even if the feature point as the tracking object disappears from the view. However, such a statistical model-based training approach usually requires an offline training stage and associated labeled training data. A second method includes tracking feature points between consecutive or adjacent frames. When adopting the latter approach, the statistical models of feature points may be dynamically updated based on the current tracking information, which handles the situations including shape deformation and intensity change adaptively. Such a tracking-based approach is fast and produces smooth trajectories. However, the tracking-based approach accumulates drifting error along the image sequence and usually leads to processing failure if the feature point as the tracking object disappears from the field of view. These two methods may also be combined to create a complex tracking methods. All of these methods, as above, may be applied to track feature portion in the application of detecting phase of physiological activities.

In some embodiments, when the similarity of the feature point and other parts of the frame where it is located is lower than a first threshold, the corresponding feature points may be tracked by the matching of image patches. As an example, when the gray level or color feature of the feature point is relatively obvious (that is, a similarity of the feature point and another point in the image is relatively low), a template matching method may be adopted. In template matching, an area around the feature point is selected as the template of the feature point, and may be later matched with other areas of the image of another frame. Various matching standards may be applied, such as cross-correlation coefficient, mutual information, and so on, but these are only non-limiting examples.

As an example, when the cross-correlation coefficient standard is used as the matching standard, this example approach may be realized as follows. In the previous frame, an independent image patch centered on the feature point may be set and the position of the independent image patch in the previous frame, such as (U, V), may be determined. In the subsequent frame, image patches with the same size may be selected within the searching area (such as (u+Δu, v+Δv)) with respect to the position (U, V) of the independent image patch in the previous frame. The convolution of the independent image patch and the selected individual patches may then be calculated as being the cross-correlation coefficient. The image patch with the largest cross-correlation coefficient may be adopted as the image patch matching with the independent image patch. Then, the difference between the positions of the two image patches may be calculated as the local motion vector of the feature point. By moving the independent image patch centered on the feature points, the local motion vector of each feature point between two adjacent frames may be calculated accordingly.

When using template matching to track feature points in adjacent frames, the template of the feature points may be updated according to the current tracking information. Such an approach may be used to deal with the situation that the morphology of feature points changes greatly over time.

In some embodiments, image patches at different scales may be used for template matching. For each scale, the template matching may generate a map with a metric score value at each sliding location. Then, the metric score maps at different scales may be merged together by performing a sum, which may be a weighted sum. By means of searching for the maximum in the merged score map, the optimal tracking position may finally be determined.

In some embodiments, the template matching may be performed at different resolutions. Specifically, as an initial aspect of template matching, an optimal matching area (i.e., the first or initial candidate area) for the feature point may be found in another frame image at a low resolution. Then, the position of the optimal matching area may be further optimized within its vicinity at a higher resolution. This process of optimal matching may be repeated until the original resolution of the image is recovered.

Figure 3:
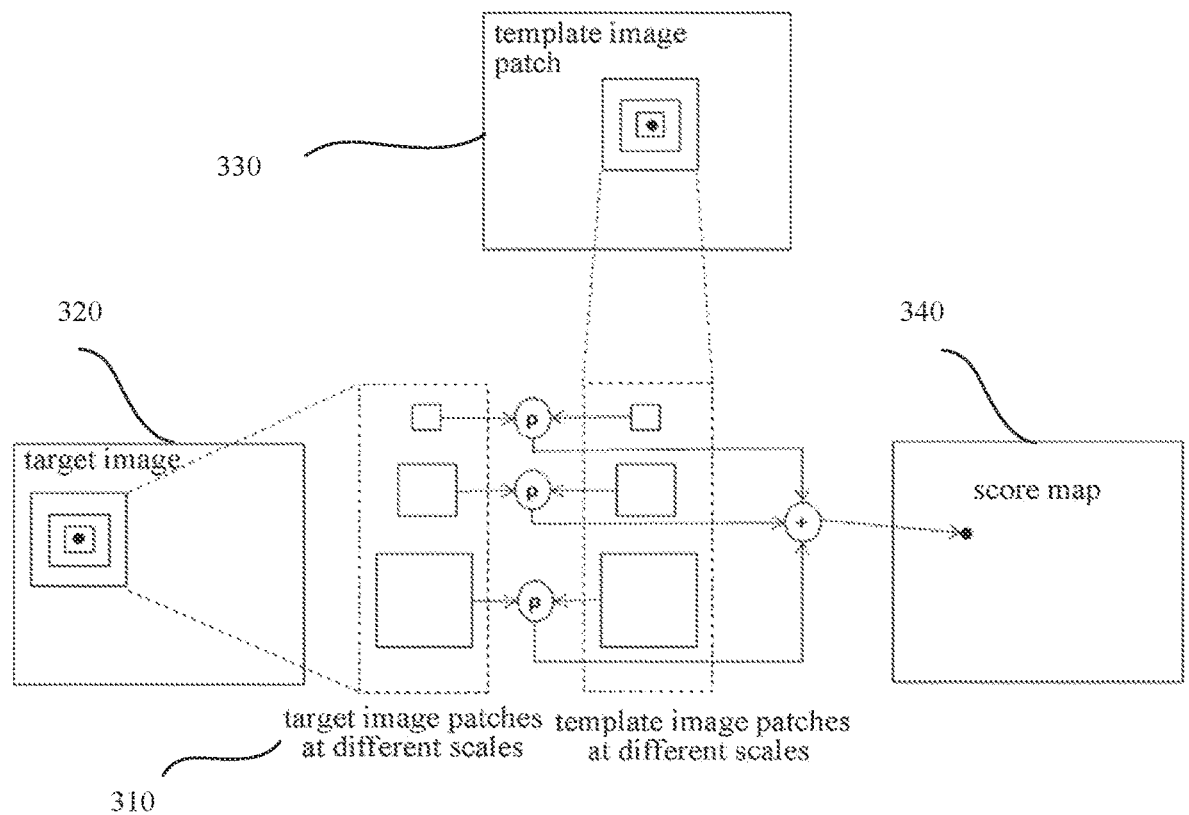
FIG. 3 is a schematic diagram showing template matching at different resolutions to track the feature portions according to an embodiment of the present disclosure.

FIG. 3 is a schematic diagram showing an example of template matching at different resolutions to track the feature portions, according to an embodiment of the present disclosure. In FIG. 3, ρ refers to a function that measures the matching extent between two image patches, with the two image patches as input. For example, a ρ function may be a square difference, a normalized square difference, a cross-correlation, a normalized cross-correlation, a cross-correlation coefficient, a normalized cross-correlation coefficient, or a normalized cross-correlation coefficient, and so on, but other p functions may be used in other embodiments. In this embodiment, as shown in FIG. 3, tracking the feature portion by template matching at different resolutions may be performed as follows. First, a series of template image patches at different scales 310 (corresponding to resolutions) may be obtained from the template image 320. Then, the template image patch with a larger scale 330 (corresponding to a lower resolution) and the target image patch at the same scale 330 selected in the target image may be input into the function p, so as to calculate the matching score between them. Then, the optimal matching area for the feature point in the target image at the present scale may be determined by searching the maximum in the merged score map 340. Next, the location of the optimal matching area may be further optimized in its neighborhood at a smaller scale (corresponding to a higher resolution). This process may be repeated until the location of optimal matching area of the feature point in the target image is determined at the original scale (corresponding to the original resolution).

By means of template matching occurring in different resolutions, the matching speed may be increased and accuracy of the matching results may be improved as well.

In other embodiments, the tracking of feature point can also be realized in the following manner. When the similarity of the feature point and other part in the frame where the feature point is located is higher than the second threshold, the corresponding feature points may be tracked independently in each frame, being based on the statistical model of the feature point.

In practice, various statistical models of a feature point may be used. For example, an image patch with a fixed size in the neighborhood of the feature point may be used as a descriptor of the feature point. In general, a feature descriptor model of the feature point may be some kind of transformation on the image patch of the feature point area. The commonly used feature descriptors include scale-invariant feature transform (SIFT) and Histogram of oriented Gradient (HOG) in the field of machine vision, as non-limiting examples. These feature descriptors may also be obtained in another manner by training convolutional neural networks (CNN) with training data as well.

In addition, the statistical model of the feature point may be combined with template matching to better track the feature points.

In certain other embodiments, a machine learning method may be used to realize the tracking of feature points. For example, a machine learning method may be used to train a classifier or metric learning model so as to detect the feature points. For example, both Support Vector Machines and Bayesian methods, such as Bayesian networks, may be used as feature point classification methods. In addition, the feature descriptor model and classification (or metric) model of feature points may be trained end-to-end by deep learning methods. In addition, deep learning based methods could be used to track the feature points.

Background Subtraction

In practice, the motion of feature points in the image is mainly affected by the integration and consideration of the following aspects. The first aspect is the periodic movement of blood vessels according to the cardiac activity. The second aspect is the periodic movement associated with respiration. The third aspect is the background movement due to non-physiological activities, such as a movement of an imaging device acquisition table by a doctor during the image acquisition. While such motion may be made in order to observe the blood vessels more clearly, leading to the occurrence of overall movement, the background motion must be considered.

Thus, the motion vectors of a feature point may be described as in the following equation:

$$V_{FeaturePortion} = V_{heart} + V_{respiratory} + V_{table}$$

In the above equation, $V_{FeaturePortion}$ is the (summed) movement of the feature point, $V_{heart}$ is the movement of the feature point caused by a heart beating, $V_{respiratory}$ is the movement of the feature point caused by respiration, and $V_{table}$ is the movement caused by non-physiological activities, as discussed in greater detail, above. In an example that a goal of the example is to determine the phase of each image frame in the cardiac cycle, the cardiac motion may be regarded as the target periodic physiological activity (that is, the periodic physiological activity to be analyzed), and the respiratory motion may be regarded as another (interfering) periodic physiological activities. Thus, it is important to determine which type of period motion is being monitored, int that different types of motion may interact and/or interfere with each other.

In an example where respiratory and non-physiological movements may be negligible, the movements of the feature point may be considered as corresponding to the vessel movement. However, depending on the scanning angle or scanning angles and the actual imaging conditions, when the movement of the feature point caused by respiratory and non-physiological movements is significant, the respiratory and non-physiological movements should be considered. In such an example, if the local motion vector of each feature point in each frame is directly analyzed using principal component analysis (PCA), the first principal component calculated may often not only be the principal motion vector corresponding to the periodic motion of the heartbeat, but also may be affected by the global motion and an offset caused by respiratory and device movement. In this example, the phase of cardiac cycles cannot be estimated accurately and directly.

In view of the above issues, one or more tracking background markers may be added as one or more fiducial markers. The movement of the fiducial marker on the image may represent the sum of the movements of the feature point on the image caused by both respiratory and non-physiological activities. Such movements are intended to be representative of motions that interfere with identifying a goal movement from the overall movement. That is to say, these movements comply with the following equation:

$$V_{fiducial} = V_{respiratory} + V_{table}$$

In the above equation, $V_{fiducial}$ is the motion of the fiducial marker on the image. Thus, the following equation may be derived from the above equation:

$$V_{heart} = V_{FeaturePortion} - V_{fiducial}$$

Specifically, in some embodiments, the local motion vector of the feature portion may be determined by the following operations. First, the displacement between the respective positions of the corresponding feature points in two adjacent frames may be calculated. Next, one or more background markers may be identified in a single frame. The periodic movement of the background markers due to the target periodic physiological activity is less than that of the feature point caused by the target periodic physiological activity. In some embodiments, the background markers may exhibit aperiodic motion (e.g., physicians may move the imaging device acquisition table) or interfering periodic motion (e.g., movement caused by respiration) caused by periodic physiological activity that is not the periodic physiological active being observed. While considering deformation of lungs during breathing may be helpful if respiration is the focus of embodiments, such deformation is unhelpful when analyzing a beating heart.

The one or more background markers may include at least a part of an anatomical structure, at least a part of an implant device, at least a part of other objects or foreign objects, etc. Specifically, in an example where cardiac motion serves as the target periodic physiological activity, the background markers may include the anatomical sites other than the lung. The lung usually moves synchronously along with the cardiac motion. Thus, the anatomical site other than the lung are therefore less affected by the cardiac motion. Such an approach can present respiratory motion and non-periodic device movement. As another example, the position of the human body with distinct image features, such as a diaphragm, may be considered as being a background markers. Alternatively, the background markers may also include a portion of an inherent foreign object in the image frame. For example, for a lung CT, the background markers may adopt part of the acquisition table in the image frame. It is to be noted that in different applications, different background markers may be selected according to the actual nature of the situation instead of limited to the examples listed above. Then, the background markers may be tracked in other frames, and the displacement of the background marker may be calculated accordingly. More specifically, the displacement between the respective positions of the corresponding background markers in two adjacent frames may be calculated. Finally, the local motion vector of the feature point may be obtained by combining the displacement of background markers. Such combining may eliminate the influence of non-target periodic physiological activities and other interfering movements. For example, the local motion vector of the feature point may be obtained by subtracting the displacement of the corresponding background marker from the displacement of the corresponding feature point.

By means of adding one or more background markers as fiducial markers to eliminate the influence of respiratory and device movements, it is possible to effectively reduce the interference of noise and other movements on periodic physiological activities. Such an approach provides the ability to perform more accurate phase analysis. At the same time, such an approach of using background markers can avoid the principal component analysis of the local motion vector that introduces the motion information of respiratory and non-physiological motions. Such motion information is useless for the subsequent phase analysis. Thus, the present approach avoids the waste of computing resources.

In the above calculation, the position $(x_i^t, y_i^t)$ of each feature point in each frame is obtained (where i represents the sequence number of the feature point and t represents the sequence number of the frame). Thus, the local motion vector of each frame for each feature point may be obtained.

Next, the process of determining the motion metric profile based on the determined local motion vector of each frame for the feature portion is described in further detail.

In some embodiments, the motion metric profile may be determined based on the determined local motion vector of each frame for the feature portion by performing the following operations. First, the principal motion vector may be extracted for each feature portion in each frame based on the principal component analysis of the local motion vector.

Then, for each frame, the global motion metric of the frame may be calculated based on the local motion vector and the principal motion vector of the frame. Finally, the motion metric profile may be determined based on the global motion metric of each frame.

Principal Motion Vector Analysis

The approach based on principal motion vector analysis is subsequently presented as an example to illustrate the determining of the phase of each frame in the image sequence based on the motion of the feature portion. However, it is to be noted that this is only a non-limiting example. For example, approaches other than extracting the principal motion vector may be adopted to track the motion characteristic information presented by the feature portions across the image sequence. Motion characteristic information may include but is not limited to motion profiles, motion parameters such as velocity, acceleration, and so on. Alternative approaches, such as averaging or integrating the motion characteristic information of each feature portion, may also be used so as to determine the phase of each frame in the whole image sequence.

Due to the non-rigid motion of a cardiovascular system with a heartbeat, there is relative displacement between multiple feature points. In order to reduce the influence of such relative displacement, principal component analysis (PCA) may be used to extract the principal motion vector of each frame of the image sequence of periodic physiological activities after the local motion vector of each frame for the feature point is obtained through the above calculation. The principle of principal component analysis is to integrate the features in the direction of maximum variance change and then highlight the vector that has the most influence on the motion of the feature points. Because the motion inclinations of multiple feature points are highly correlated with one another, the result based on the principal motion vector may be regarded as the global motion metric of each frame. Using such a result may characterize the global change of the image sequence of periodic physiological activities.

The following takes a coronary angiography (CAG) image sequence as an example to illustrate the particular process of principal component analysis.

In a CAG image sequence, coronary vessels and catheters are the most important moving objects. Under normal image acquisition conditions, the movement and deformation of vessels and catheters in the image are mainly caused by a heartbeat. Thus, the first principal component in the result of principal component analysis corresponds to the periodic movement of the heartbeat.

Specifically, $M^t$ may be used to represent the motions of feature points in frame t, which is the collection or set of motions of each feature point in the frame. Assuming $M^t=\{(u_i^t, v_i^t), i=1, \ldots, n\}$, where n is the number of feature points, $(u_i^t, v_i^t)$ denotes the motion in the (x,y) direction of the $i^{th}$ feature point. The values of $(u_i^t, v_i^t)$ may be obtained by calculating the difference as follows: $u_i^t = x_i^t - x_i^{t-1}$, $v_i^t = y_i^t - y_i^{t-1}$.

For convenient subsequent analysis, the elements in $M^t$ may be expanded, in sequence, into a one-dimensional vector with length of 2n, which is denoted as $EM^t$. For example: $EM^t = (u_0^t, v_0^t, u_1^t, v_1^t, \ldots, u_n^t, v_n^t)$.

One-dimensional vectors EMs of the N frames of the image sequence may be combined to get a high dimensional motion vector, which may be denoted as $D = \{EM^t, t=1, \ldots, N\}$, where N is the sequence number of the frame. D is a matrix with dimension of (2n)×N. In this way, by using principal component analysis, the eigenvector corresponding to the maximum eigenvalue of the high-dimensional motion vector, also known as the first principal component or principal motion vector, denoted as X, may be obtained, according to the following Equation 1:

$$X^* = \arg\max_{\|x\|=1} \mathrm{var}(D^T X) \quad \text{(Equation 1)}$$

The principal motion vector X* represents the direction and magnitude of the most principal motion change of the feature points, also known as the principal motion direction and magnitude. The direction of the principal motion vector may be inverted as needed, to be consistent with a desired positive direction as defined in specific application settings.

Principal component analysis (PCA) may filter out a part of influence of the background noise, especially static noises. Compared with the existing methods that only calculate the image difference between different frames and the method based on reference image comparison, PCA is less susceptible to the influence of background noises.

PCA may be implemented using various approaches. For example, linear decomposition or nonlinear decomposition may be used to perform principal component analysis. In some embodiments, such as in the application of coronary angiography, in the case of a normal timing sampling rate (for example, the speed of 15 frames per second), the principal component analysis based on linear decomposition may get the principal component of motion. Thus, PCA may interpret the cardiac motion well. Compared with using a non-linear decomposition for PCA, using the linear decomposition for PCA consumes fewer computing resources with a faster computing speed, while still providing helpful results.

For example, PCA may be implemented using linear matrix decomposition, such as singular value decomposition (SVD) or eigenvalue decomposition (EVD) as non-limiting examples.

For example, with SVD, the matrix D may be decomposed into, as per Equation 2:

$$D = USV^T \quad \text{(Equation 2)}$$

In Equation 2, U and V are both orthogonal matrices, and S is a diagonal matrix. The principal component of PCA (also known as the principal motion vector) X* is found as the first column vector of V.

Furthermore, for other applications, if PCA does not work well in reducing the dimension of superposition of different motions, nonlinear dimensionality reduction methods may also be adopted. Examples of such methods include Kernel PCA and Deep Belief Network, and so on, as non-limiting examples. In addition, the principal motion vector could be pre-defined for simplicity, without solving the equation. For example, the principal motion vector could be defined by the head-to-toe direction or one specific direction in the image (y axis direction as an example).

Global Motion Metric Reconstruction and Phase Estimation

For each frame, based on the local motion vector and principal motion vector of the frame as calculated above, the global motion metric of the frame corresponding to the periodic cardiac motion may be calculated.

In some embodiments, for each frame, the global motion metric m(t) corresponding to the frame may be obtained by projecting the local motion vector of the frame onto the principal motion vector using a dot product, as in Equation 3, below:

$$m(t) = \mathrm{dot}(X^*, X^t) \quad \text{(Equation 3)}$$

In Equation 3, the vector X* is the principal motion vector, and $X^t$ is the local motion vector of frame t.

In other embodiments, in order to eliminate the effect of a magnitude of the principal motion vector during projection, the above projection may be divided by the modulus or magnitude of the corresponding principal motion vector to obtain the global motion metric m(t) corresponding to each frame, as shown in Equation 4:

$$m(t)=\text{dot}(X^*,X^t)/|X^*| \quad \text{(Equation 4)}$$

Next, after getting the global motion metric of each frame, the global motion metrics of the respective frames may be drawn directly into a profile, such as the global motion metrics profile. Alternatively, the global motion metrics profile may be determined by integrating the global motion metrics of the previous frames with respect to each frame. Furthermore, the phase of the frame in the image sequence may be determined based on the global motion metric profile. The particular process of determining the global motion metric profile and phase estimation is described in further detail, below.

Figure 4A:
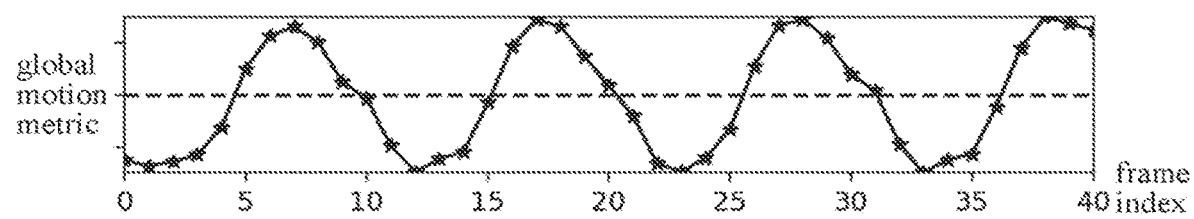
FIG. 4A illustrates a profile of the global motion metric of a coronary angiography image sequence obtained according to an embodiment of the present disclosure.

FIG. 4A illustrates a diagram of the global motion metrics profile of coronary angiography image sequence, according to an embodiment of the present disclosure. In FIG. 4A, the horizontal axis represents the sequence number of the frame, and the vertical axis represents the global motion metric.

The phase of each frame in the periodic physiological activity may be calculated based on the global motion metric of each frame. For example, different cardiac phases correspond to different motion characteristics, as shown in Table 1, below:

TABLE 1

Motion Description of Cardiac Phase

| Cardiac Phase | Characteristics of Corresponding Global Motion Metric |
| --- | --- |
| Isovolumetric contraction phase | Contraction at low pace |
| Fast outflow phase | Rapid contraction |
| Slow outflow phase | Continued contraction at lower pace |
| Isovolumetric relaxation phase | Transition from contraction to relaxation |
| Fast filling phase | Rapid relaxation |
| Slow filling phase | Continued relaxation at lower pace |
| Ventricular systole | Transition from relaxation to contraction |

As shown in FIG. 4A, global motion intensity with a positive value in the longitudinal y-axis represents diastolic motion, and global motion intensity with a negative value in the longitudinal y-axis represents systolic motion. Here, diastolic motion refers to motion where the heart fills and systolic motion refers to motion where the heart empties. The magnitude of global motion intensity indicates the instantaneous velocity of the motion. For example, a zero-crossing point with a positive slope indicates that the global motion metric is changing from systolic motion to diastolic motion, and the vicinity of such a point is the end of ventricular systole. A zero-crossing point with a negative slope indicates that the global motion metric is changing from diastolic motion to systolic motion, and the vicinity of such a point is the end of ventricular diastole.

In some embodiments, after determining the end of a ventricular systole period and a ventricular diastole period, the entirety of the cardiac cycle interval may be mapped out. According to the distribution proportions of each phase in the cardiac cycle, the corresponding cardiac phase of each frame may be determined. The physical phase of each frame in the interval of [0, 2π] may be inferred thereafter.

Figure 4B:
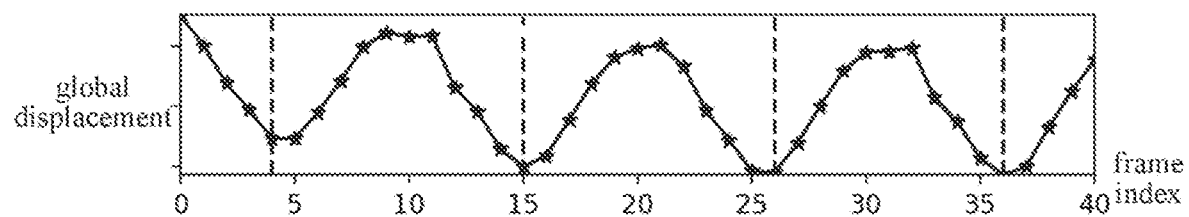
FIG. 4B illustrates a profile of the global displacement of coronary angiography image sequence obtained according to another embodiment of the present disclosure.

In other embodiments, in order to further improve the accuracy of cardiac phase estimation, the global motion intensity m(x) may be integrated in time (see Equation 5, below), to obtain a profile of global displacement d(t) for each frame, as shown in FIG. 4B.

$$d(t)=\int_0^t m(x)dx \quad \text{(Equation 5)}$$

In FIG. 4 B(b), the horizontal x-axis indicates a frame index and the longitudinal y-axis indicates a magnitude of global displacement. From FIG. 4B, the period of motion may be estimated and the corresponding cardiac phase of each frame may be determined, accordingly. For example, in FIG. 4B, in addition to referring to the slope and zero crossing points mentioned above, it may be further concluded that the peak corresponds to an end of a diastole period, and the trough corresponds to an end of a systole period.

In some embodiments, after determining the end of a ventricular systole period and a ventricular diastole period, or after determining the adjacent ends of a ventricular systole period (or adjacent ends of a ventricular diastole period), the whole cardiac cycle interval may be determined, accordingly. Based on the distribution proportion of each phase in the cardiac cycle, the corresponding cardiac phase of each frame may be determined, and the physical phase of each frame in the interval of [0, 2π] may be inferred thereafter. Such an interval may reflect a complete cardiac cycle.

The technology of the present disclosure is not limited to the clinical application of coronary angiography. In general, the technology of the present disclosure may be extended to the analysis of periodic sequential images in other computer vision fields. For example, the whole analysis process may be applied to the 4-D computerized tomography (CT) image sequence of periodic respiratory motions of a lung. Here, 4-D indicates that the image sequence represents a 3-D model that changes over time. However, this is only a non-limiting example. When the image sequence is 4-D, each frame is a 3-D image.

Figure 5:
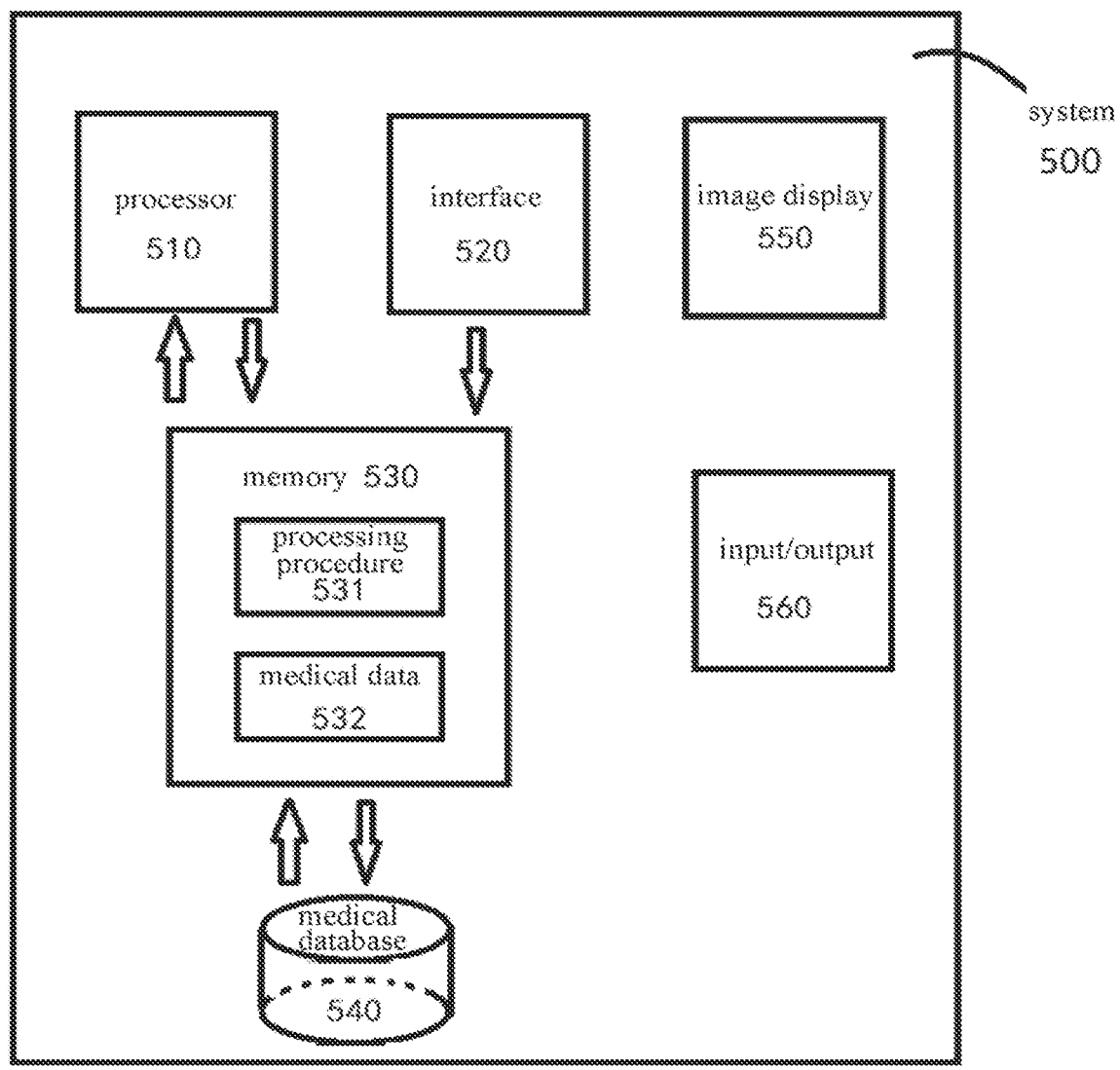
FIG. 5 illustrates a system for analyzing an image sequence of a periodic physiological activity according to another embodiment of the present disclosure.

FIG. 5 is a diagram showing a system for analyzing an image sequence of a periodic physiological activity, according to yet another embodiment of the present disclosure. As is understood by those skilled in the art, in some embodiments, the system 500 may be a dedicated intelligent device or a general intelligent device. For example, the system 500 may be a computer customized for use by a hospital to process image data acquisition and image data processing tasks, or a cloud server that may provide such functionality. For example, the system 500 can also be integrated into an imaging device that acquires image sequences for patients, for example, in a digital subtraction angiography (DSA) imaging device, a lung CT imaging device, and the like, as non-limiting examples.

The system 500 may include a processor 510 and an interface 520. Alternatively, as shown in FIG. 5, the system 500 may additionally include at least one of a memory 530, a medical database 540, an input/output 560, and an image display 550. However, the system 500 may not include all of these enumerated elements and may include other elements in other embodiments.

The processor 510 may be a processing device including one or more general-purpose processing devices such as a microprocessor, a central processing unit (CPU), a graphics processing unit (GPU), etc. More specifically, the processor 510 may be a complex instruction set operation (CISC)

microprocessor, a reduced instruction set operation (RISC) microprocessor, a very long instruction word (VLIW) microprocessor, a processor running other instruction sets, or a processor running a combination of instruction sets, as non-limiting examples. The processor 510 may also refer to one or more dedicated processing devices such as an application specific integrated circuit (ASIC), a field programmable gate array (FPGA), a digital signal processor (DSP), a system on chip (SOC), as non-limiting examples.

The interface 520 is configured to receive an image sequence acquired by the imaging device having a plurality of frames. The interface 520 may include a network adapter, a cable connector, a serial connector, a USB connector, a parallel connector, a high-speed data transmission adapter such as an optical fiber, a USB 3.0 adapter, a LIGHTNING adapter, a wireless network adapter such as a WI-FI adapter, a telecommunication adapter (such as 3G, 4G/LTE, etc.), etc. The system 500 may be connected to the network through the interface 520.

The processor 510 may be communicatively connected to the storage 530 and configured to execute computer executable instructions stored therein. The storage 530 may include a read only memory (ROM), a flash memory, a random-access memory (RAM), a static memory, and the like, as non-limiting examples. In some embodiments, the storage 530 may store computer executable instructions, such as one or more processing procedure 531, and medical data 532 generated while executing the computer programs. The processor 510 may execute the processing procedure 531 to implement the steps of the image sequence analysis method for periodic physiological activity described in combination with FIG. 1. Alternatively, when the processor 510 executes the processing procedure 531, the method for determining the local motion vector of each frame for the feature portion described above may be implemented. Alternatively, the processor 510 may execute the processing procedure 531 to realize the method described above for determining the motion metric profile based on the determined local motion vector of each frame for the feature portion. Alternatively, the processor 510 may execute the processing procedure 531 to implement each step of the phase estimation described in combination with FIG. 4A and FIG. 4B, including the steps for projecting the local motion vector of each frame for each feature portion to its principal motion vector to obtain the global motion metric, and determining the phase of each frame based on the global motion metric. In some embodiments, the processing procedure 531 also includes the steps of determining the global displacement based on the global motion metric and determining the phase of each frame based on the global displacement, and so on.

The processor 510 may also send/receive medical data 532 to/from the storage 530. For example, the image sequence acquired through the interface may be stored in the storage 530. The image sequence may be retrieved from the storage 530 when the processor 510 executes the processing. In some embodiments, when the processor 510 executes the processing procedure 531, the estimated phase may be marked on the corresponding image frame. Then, the image frame marked with the phase may be transferred to the storage 530. Alternatively, the storage 530 may communicate with the medical database 540 to acquire image sequences from the medical database 540 or transmit image frames marked with phase into the medical database 540 for retrieval and use by users authorized to access the medical database 540.

The medical database 540 is optional and may include multiple devices located in a centralized or distributed manner, such as over a cloud network. The processor 510 may communicate with the medical database 540 to read image sequences into the storage 530, or store image sequences from the storage 530 into the medical database 540. Alternatively, the medical database 540 may also store the image sequences to be phase estimated, and in such an example the processor 510 can communicate with the medical database 540, transmit and store the phase marked image to the storage 530, and display the phase marked image on the display 550, so that a doctor can use the input/output 560 to label the phase marked image by professional software, and enable (one or more) processing procedures to construct the data set for three-dimensional reconstruction. For example, two-dimensional images are grouped according to the phases, and the two-dimensional images in the same group are images with the same phase or different but similar or close projection angles, which may be used for three-dimensional reconstruction together.

The input/output 560 may be configured to allow data to be received and/or transmitted by the system 500. The input/output 560 may include one or more digital and/or analog communication devices that allow the system 500 to communicate with users or other machines and devices. For example, the input/output 560 may include a keyboard and mouse that allow the user to provide input.

In addition to displaying medical images, the image display 550 can also be used to display other useful information, such as the phase of the image in the physiological cycle activity. For example, the image display 550 may be an LCD, CRT, or LED display, as non-limiting examples.

This disclosure describes various operations or functions that may be implemented or defined as software codes or instructions. Such content may be directly executable ("object" or "executable" form) source code or differential code ("incremental" or "patch" code). The software implementation of the embodiments described herein may be provided via a product in which codes or instructions are stored, or in manner of data transmission via the communication interface, through the operation of communication interface. A machine or computer-readable storage medium may cause a machine to perform the described functions or operations. Such a medium may include any mechanism for storing information in form of accessible by a machine, for example (e.g., computing devices, electronic systems, and so on). For example, the computer-readable storage medium may be a recordable or a non-recordable medium (e.g., read only memory (ROM), random access memory (RAM), disk storage medium, optical storage medium, flash devices, etc.). The communication interface includes any mechanism that is connected to any one of hardwired, wireless, optical and or a similar medium to communicate with another device, such as a memory bus interface, a processor bus interface, an Internet connection, a disk controller, and so on, as non-limiting examples. The communication interface may be configured to be prepared to provide data signals describing software content, by providing configuration parameters and/or by transmitting signals. The communication interface may be accessed via one or more commands or signals sent to the communication interface.

The present disclosure also relates to a system for performing the operations herein. The system may be specially constructed for a desired purpose, or the system may include a general-purpose computer selectively activated or reconfigured by executing or performing a computer program stored in the computer. Such a computer program may be stored in a computer-readable storage medium such as, but not limited to, any type of disk including a floppy disk, an optical disk, a CDROM, a magneto-optical disk, a read-only memory (ROM), a random access memory (RAM), an EPROM, an EEPROM, a magnetic card or an optical card, or any type of medium suitable for storing electronic instructions, where the computer-readable storage medium is coupled to the bus of the computer system.

The various aspects of the present invention have been described in detail, and it is obvious that modifications and variations are possible without departing from the scope of the invention as defined in the appended claims. Since various changes to the above-described structures, products, and methods can be made without departing from the scope of the present invention, it is intended that all of the contents included in the above description and shown in the drawings should be construed as exemplary without restrictive meaning.

What is claimed is:

1. A computer-implemented method for analyzing an image sequence of a periodic physiological activity, the method comprising:
   receiving the image sequence acquired by an imaging device, the image sequence including a plurality of images;
   identifying at least one feature portion in a selected image of the image sequence, the at least one feature portion moving responsive to the periodic physiological activity;
   detecting, by a processor, the corresponding feature portions in other images of the image sequence; and
   determining, by the processor, a phase of the selected image in the image sequence based on the motion of the feature portion.

2. The computer-implemented method of claim 1, wherein the determining a phase of the selected image in the image sequence based on the motion of the feature portion further comprises:
   determining local motion vectors of each image for the feature portions;
   determining a motion metric profile based on the determined local motion vectors of each image for the feature portions; and
   determining the phase of the selected image in the image sequence based on the determined motion metric profile.

3. The computer-implemented method of claim 1, wherein the identifying the feature portion further comprises identifying either one or both of a specific region of an anatomic structure and another object in the image as the feature portion.

4. The computer-implemented method of claim 1, wherein the detecting the corresponding feature portions in other images of the image sequence comprises at least one of the following:
   detecting the corresponding feature portions using image patch matching;
   detecting the corresponding feature portions independently in each image based on a statistical model of the feature portion; or
   detecting the corresponding feature portions using a machine learning method.

5. The computer-implemented method of claim 1, wherein the at least one feature portion comprises a plurality of critical areas.

6. The computer-implemented method of claim 2, wherein the determining a motion metric profile based on the determined local motion vectors of each image for the feature portions further comprises:
   extracting a principal motion vector for each feature portion in each image based on principal component analysis of the local motion vectors, or using a predefined principal direction;
   calculating global motion metric for each image based on the local motion vectors and the principal motion vector of the corresponding image; and
   determining a motion metric profile based on the global motion metric for each image.

7. The computer-implemented method of claim 6, wherein the determining a motion metric profile further comprises one of:
   integrating the global motion metric for the prior images of each image to determine a global motion metric profile for the respective image; or
   using the global motion metrics for the plurality of images as the global motion metric profile.

8. The computer-implemented method of claim 2, wherein the determining local motion vectors for the feature portions further comprises:
   calculating a displacement between the respective locations of the corresponding feature portions in two adjacent images;
   identifying a background marker in the image, the background marker having less periodic movement due to the periodic physiological activity than that of the feature portion;
   tracking the background markers in the other images;
   calculating a displacement of each of the background markers; and
   obtaining the local motion vectors for the feature portions by combining the displacements of the background markers.

9. The computer-implemented method of claim 8, wherein the background markers further comprise at least one of: at least a part of anatomic structures, at least a part of implanted devices, or at least a part of other objects.

10. The computer-implemented method of claim 8, wherein the physiological activity comprises cardiac motion.

11. The computer-implemented method of claim 1, further comprising identifying a fiducial marker and using the position of the fiducial marker to identify and correct for a motion due to at least one of a periodic physiological activity not being analyzed or a non-physiological motion.

12. A system for analyzing an image sequence of periodic physiological activity, comprising:
   an interface, configured to receive the image sequence acquired by an imaging device, the image sequence including a plurality of images;
   a processor, configured to:
   identify at least one feature portion in a selected image of the image sequence, the at least one feature portion moving responsive to the periodic physiological activity;
   detect the corresponding feature portions in other images of the image sequence; and
   determine a phase of the selected image in the image sequence based on the motion of the feature portions.

13. The system of claim 12, wherein the processor is further configured to:
   determine local motion vectors of each image for the feature portions;
   determine a motion metric profile based on the determined local motion vectors of each image for the feature portions; and determine the phase of the selected image in the image sequence based on the determined motion metric profile.

14. The system of claim 12, wherein the processor is further configured to identify the feature portion by identifying either one or both of a specific region of an anatomic structure and another object in the image as the feature portion.

15. The system of claim 12, wherein the processor is further configured to detect the corresponding feature portions by performing at least one of the following:
   detecting the corresponding feature portions using image patch matching;
   detecting the corresponding feature portions independently in each image based on a statistical model of the feature portion; or
   detecting the corresponding feature portions in other images of the image sequence using a machine learning method.

16. The system of claim 13, wherein the processor is further configured to determine local motion vectors for the feature portions by performing the following:
   calculating a displacement between the respective locations of the corresponding feature portions in two adjacent images;
   identifying background markers in the image, the background marker having less periodic movement due to the periodic physiological activity than that of the feature portions;
   tracking the background markers in the other images;
   calculating a displacement of each of the background marker; and
   obtaining the local motion vectors for the feature portions by combining the displacements of the background markers.

17. The system of claim 12, wherein the background markers further comprise at least one of at least a part of anatomic structures, at least a part of implanted devices, or at least a part of other objects.

18. The system of claim 12, wherein the physiological activity comprises cardiac motion.

19. The system of claim 12, wherein the processor is further configured to identify a fiducial marker and use the position of the fiducial marker to identify and correct for a motion due to at least one of a periodic physiological activity not being analyzed and a non-physiological motion.

20. A non-transitory computer-readable storage medium, with computer-executable instructions stored thereon, wherein the instructions, when executed by a processor, cause the processor to perform a method for analyzing an image sequence of a periodic physiological activity, the method comprising:
   receiving the image sequence acquired by an imaging device, the image sequence including a plurality of images;
   identifying at least one feature portion in a selected image of the image sequence, the at least one feature portion moving responsive to the periodic physiological activity;
   detecting the corresponding feature portions in other images of the image sequence; and
   determining a phase of the selected image in the image sequence based on the motion of the feature portion.

* * * * *